United States Patent [19]

Beutler et al.

[11] Patent Number: 4,808,388
[45] Date of Patent: Feb. 28, 1989

[54] FOAMABLE CREAMS

[75] Inventors: Rolf D. Beutler; Thomas Wimmer, both of Frankfurt am Main; Gunhild Angst, Bad Camberg, all of Fed. Rep. of Germany

[73] Assignee: Merz + Co. GmbH & Co., Frankfurt, Fed. Rep. of Germany

[21] Appl. No.: 86,565

[22] Filed: Aug. 18, 1987

[30] Foreign Application Priority Data

Aug. 20, 1986 [DE] Fed. Rep. of Germany ....... 3628531

[51] Int. Cl.$^4$ ............................................... A61K 7/00
[52] U.S. Cl. ....................................... 424/47; 424/71; 514/941; 514/943; 514/945
[58] Field of Search ................... 424/47, 71; 514/943, 514/945, 941

[56] References Cited

U.S. PATENT DOCUMENTS 3,970,584 7/1976 Hart et al. .............................. 424/47
4,035,513 7/1977 Kumano ............................... 514/941
4,254,104 3/1981 Suzuki ................................. 514/941

Primary Examiner—Thurman K. Page
Assistant Examiner—P. Prater
Attorney, Agent, or Firm—Gordon W. Hueschen

[57] ABSTRACT

Foamable cosmetic creams for application onto the skin, comprising a selected creamy oil-in-water emulsion and a selected propellant, which may be and advantageously is a single propellant gas, are disclosed. Improvement of the froth properties is effected by predetermined control of the ingredients of the composition and their proportions, comprising specific percentage ranges of nonionic emulsifier, oil portion, consistency-providing agent, and water, a viscosity of the starting cream emulsion formed therefrom between about 200 and 500 mPas, and the propellant employed, which consists essentially of nitrous oxide or carbon dioxide, preferably nitrous oxide.

7 Claims, No Drawings

FOAMABLE CREAMS

BACKGROUND OF THE INVENTION

1. Field of Invention

The present invention is concerned with dermatologically-acceptable creams, which are foamable by means of an included propellant from a dispenser vial or other dispensing container, for application onto the skin in the form of a cosmetic mousse.

2. Prior Art

The requirements placed upon this type of cream or lotion, in particular, are an adequate foam stability, fluffy and creamy consistency, bright and non-dull appearance, easy distributability, and ready absorption by the skin. In practice, the major difficulties heretofore encountered have resided in the problem of combining all of these properties into a single product without sacrificing one advantage for the other.

Attempts have already been made to solve this problem by employing special gases, particularly combinations thereof, as essential propellants in specific and limited predetermined weight ratios (DE-PS No. 24 06 109 and corresponding U.S. Pat. No. 3,970,584, issued July 20, 1976 to S. C. Johnson and Son).

The invention of the Johnson patent involves a mixture of two physicochemically different propellant systems, namely, a pressurized gas such as $CO_2$, $N_2O$, $O_2$, or $N_2$, which must be mixed with a liquified gas such as a hydrocarbon or halogenated hydrocarbon. The Johnson formulation will, however, not lead to a usable product if only one propellant-type is used alone, which would be an obvious advantage. Moreover, if a liquified gas is used as propellant, no satisfactory product, as desired according to the present invention, is delivered from the container in which the emulsion of the invention is dispensed.

OBJECTS OF THE INVENTION

It is an object of the invention to provide an improved dermatologically-acceptable foam- or mousse-producing composition which is a creamy oil-in-water emulsion comprising certain prescribed components with certain ranges as well as certain prescribed physical characteristics which moreover requires only a single pressurized gas to convert it from the creamy emulsion to the dispensed mousse. Another object is the provision of such a product wherein nitrous oxide or carbon dioxide, preferably the former, is the essential single propellant involved. Other objects will become apparent hereinafter and still others will be obvious to one skilled in the art.

SUMMARY OF THE INVENTION

It has now been found that the properties of such foams can be substantially improved, attaining, in particular, a bright and creamy froth or mousse which is stable for at least five (5) minutes if—irrespective of the particular propellant employed—the cream emulsion, loaded into the dispensing container and to be therein mixed with the propellent, comprises a predetermined combination of ingredients making up the composition and predetermined physical parameters therefor, with such improvement being obtained with the employment of either of two suitable and selected propellants, although the greatest improvement is achieved by the selection of a particular propellant, namely, nitrous oxide.

The present invention preferably employs pressurized nitrous oxide alone, which has been found to give best results. If $CO_2$, another compressed gas, is used, the resulting mousse is satisfactory, but not as outstanding or advantageous, as can be seen from the examples. Both $N_2O$ and $CO_2$ show a sufficient solubility in the water of the emulsion system and otherwise fulfil the requirements of the present invention. If $O_2$ and $N_2$, which are compressed gases which theoretically could also be used, are employed, however, no mousse with suitable properties is delivered from the dispenser because, among other things, of the lack of adequate solubility of these gases in water.

The present invention therefore utilizes the essential employment of $N_2O$ or $CO_2$ alone, preferably $N_2O$. Of course, this does not mean that the addition of small amounts of other and even otherwise unsuitable gases will alter the characteristics of the product so much as to avoid the operativeness or advantages of the present invention, as will be recognized by one skilled in the art, and to this extent small amounts of other gases may be included, as more fully disclosed hereinafter.

THE INVENTION IN GENERAL

The starting emulsion according to the invention contains between about 2 and 9 percent by weight of nonionic emulsifying agent, between about 4.5 and 21 percent by weight of oil portion, and between about 0.5 and 4.5 percent by weight of consistency-providing agent, the balance being water to 100 percent by weight, and it must have a viscosity of between about 290 and 500 mPas (as measured on the ROTOVISKO ™ viscometer of the Haake Company, West Germany, MVI system, measuring head 500, 64 rpm at 25° C.).

(A) The nonionic wetting agent employed can be, for example, an alkyl polyglycol phosphoric acid ester, glyceryl stearate, PEG glyceryl stearate, PEG stearate, PEG stearyl or PEG cetyl stearyl ether, each by itself or in combination with one another.

(B) The oil porton is selected, for example, from fatty substances such as vegetable and mineral oils, liquid fatty alcohols, and liquid waxes.

(C) The consistency-providing agent suitably employed may be, for example, selected forom macromolecular gel builders, fats, waxes, and alcohols of long-chain fatty acids.

In addition to selecting the emulsion components and adhering to the critical quantity ranges as above-stated, in the practice of the invention it is also important to adjust the emulsion before mixing with the selected propellant into the afore-mentioned viscosity ranges, i.e., the viscosity of the cream emulsion not yet mixed with the foaming agent or propellant must have the specified viscosity. Unless these viscosity values are adhered to, the properties of the foamed cream will not be entirely satisfactory despite adherence to the quantity ranges of the emulsion as specified for the invention. It is apparent that the viscosity of the emulsion is determined by its composition, i.e., by its components and the quantity ratios thereof. Therefore, in case it should first turn out in respect of any particular emulsion, prepared within the specified ranges of the invention, that it does not have the viscosity values specified for the invention, then amounts of the respective components will have to be altered so as to bring the viscosity within the ranges specified for the invention to be operative.

The viscosity of the starting oil in water emulsion has an important influence, along with the type of propellant employed, upon the foam density and the bubble size of the cream froth. What is desired is a foam density between about 0.1 and 0.16 g/cm$^3$ and an average bubble size of between about 4 and 20 $\mu$m. In this respect, both viscosity of the starting emulsion and the propellent employed are critical.

The particularly preferred propellant is nitrous oxide ($N_2O$). However, carbon dioxide or mixtures of nitrous oxide with carbon dioxide, nitrogen, or fluorohydrocarbons may also suitably be employed. If propellant mixtures are used, the following weight ratios are preferred, it being observed from the examples that the propellant must consist essentially of nitrous oxide or carbon dioxide, with nitrous oxide being much preferred. Within the limits of "consisting essentially of", for nitrous oxide, it is to be understood that the following mixtures are to be included, as well as a mixture of carbon dioxide or nitrous oxide with minor amounts of any other propellant which does not detract from the desired and superior resulting foam product:
nitrous oxide:carbon dioxide = 1:0.5–1
nitrous oxide:fluorohydrocarbon = 1:0.8–0.9
nitrous oxide:nitrogen = 1:0.5–1

FURTHER DISCUSSION OF COMPONENTS

The components of the formulations of the present invention may be characterized by their galenical task in the product. Therefore a nonionic emulsifier (A), an oil portion (B), a so-called consistency-providing agent (C), and water (D) are the essential ingredients or components. The nonionic emulsifier (A) employed is selected so as to be dermatologically acceptable, since the product is intended for skin care. As is usual in the development of emulsion systems, at least two different types of emulsifiers are preferably and normally employed to give the emulsion improved physical stability. One emulsifier alone may be sufficient, as shown in Example 4/1, although such is not the usual practice.

In emulsion type products for skin care the content of fats and fatty substances is normally adjusted to between about 15 and about 30% by weight, depending upon the skin status. Even when nonionic-emulsifiers are counted as fat components, we have generally been able to satisfy this requirement by operating according to the present invention, it being recognized that from a dermatological and economic point of view, it is not worthwhile or desirable to extend the amount of emulsifier employed beyond what is required for a stable emulsion. The rest of the fat is provided by liquid oils and fats—here named "oil portion (B)"—which have no surface activity as does component (A), and essentially no consistency-providing characteristics as does component (C).

Even if a nearly satisfactory emulsion system can be produced using components A, B and water (D) alone, the consistency-providing component (C) is necessary to increase the viscosity to the desired and necessary range of 200–500 mPas and to ensure the desired product foam-forming characteristics and enhance the foam appearance and stability. It is for this reason that the so-called consistency-providing agent (C) is employed. One can utilize solid fats such as the higher fatty alcohol Cetearyl Alcohol, as well as Paraffin oil, or solid waxes. On the other hand, materials such as a carboxy-containing polymer, e.g., Cabomer 940 (neutralized with triethanolamine, sodium hydroxide solution, or ammonia water) or traganth or other gum may also be used as component (C).

The starting emulsion may be prepared as shown in working Example 1, or otherwise according to the skill of the art for preparing such oil-in-water emulsions and charging them with a propellant gas, illustratively according to U.S. Pat. No. 3,970,584, to which reference may also be made for other details which are well known to one skilled in the art.

DISCUSSION OF THE EXAMPLES

The examples show that, to achieve a suitable creamy, shiny foam suitable as a cosmetic mousse and having a proper foam stability and density, using essentially a single gaseous propellant, which consists essentially of nitrous oxide or carbon dioxide, the following parameters must be recognized in practice:

The emulsion must consist essentially of the following in intimate admixture:

| ingredient | weight percent (or parts) |
|---|---|
| (a) nonionic emulsifying agent | 2–9 |
| (b) oil portion | 4.5–21 |
| (c) consistency-providing portion | .5–4.5 |
| (d) water | q.s. 100, | said emulsion having a viscosity between about 200 and 500 mPas, with which emulsion in a suitable dispensing container with usual dispensing nozzle is then combined the specified propellant gas, usually in the range of between about one and four percent by weight of total propellant-containing emulsion, preferably between about 1.2 and 3.2 percent, and ordinarily to give a pressure between about 7 and 10 bar or 100 and 150 psi in the dispensing container. When the propellant is essentially $N_2O$, the range is preferably between about 2 and 3.2 percent, and when the propellant is essentially $CO_2$, the range is preferably between about 1.2 and 1.7 percent.

The Examples show that, when the nonionic emulsifier is not present within the prescribed range, the results are not satisfactory, even when other types of emulsifier are also present; that the selection of the propellant is critical; that viscosity values for the starting emulsion are critical and that other types of emulsifying agents can actually detract from or prevent the production of a satisfactory emulsion and mousse if employed in too great a quantity along with the necessary nonionic emulsifying agent; and that an essentially single gas propellant will not be effective to produce a satisfactory emulsion and foam mousse unless all of the foregoing parameters are recognized and followed in practice.

DETAILED DESCRIPTION OF THE INVENTION

The following Examples are given by way of illustration only and are not to be construed as limiting, all ingredients or components being identified by the CTFA nomenclature as evidenced by the CTFA—Cosmetic Ingredient Dictionary, 3rd Edition (1982), published by The Cosmetic, Toiletry and Fragrance Assoc., Inc., 1110 Vermont Ave. N.W., in Washington, DC, 20005.

EXAMPLE—REPESENTATIVE WORKING EXAMPLE

An oil-in-water emulsion system having the following formulation is charged with nitrous oxide as propellant system:

| | | |
|---|---|---|
| (A) | Trilaureth-4-Phosphate | 2.0 g |
| | Polyglyceryl-2-PEG-4-stearate | 6.0 g |
| | Cetearth-12 | 1.0 g |
| (B) | Mineral Oil | 6.0 g |
| | Avocado Oil | 1.0 g |
| | Isopropyl Palmitate | 5.0 g |
| | Jojoba Oil | 1.0 g |
| | Octyldodecanol | 3.0 g |
| (C) | Cetearyl Alcohol | 2.0 g |
| | Carbomer 940 | 0.3 g |
| (D) | Water | 72.3 g |
| | Triethanolamine 99% | 0.4 g |

Mix A, B and the Cetearyl Alcohol of C and heat this mixture to about 70° C. (158° F.). Add the Carbomer 940 and disperse carefully by stirring the melt. Heat D to about 75° C. (167° F.) and add this solution in parts to the melt while stirring. After addition of total amount of D, stir for about 10 minutes. Then cool the resulting emulsion to about 28° C. (82.4° F.).

Homogenise in usual manner with a suitable system for about five minutes at 1500 rpm. Homogenisation in context with emulsion systems is very common. A representative homogenizer system is called ULTRA TURRAX TM by Ika-Werk, Janke and Kunkel, D-7813 Staufen im Breisgau. The distribution of the water particles in the oil-water system is thus enhanced, the particles become smaller, and the system becomes more stable.

The principles of such a homogenizer is a rapidly-rotating stirring device within a static one. The necessary degree of distribution is determined by the time (usually about 5 minutes) and the speed (usually about 1500 rpm, revolutions per minute) during usage. Suitable substances (preservative, perfume, or cosmetically-active ingredient) may be added during the production process.

Then 47.6 g of the emulsion is charged with 1.4 g pressurized nitrous oxide. The results are as shown in the Table for Example 1/1a.

The other compositions set forth in the Table are prepared in the same manner or with modifications which will be apparent to one skilled in the art and are similarly identified by a distinctive Example number in the heading.

Example 1/1a

| 1. | Ingredients | | |
|---|---|---|---|
| (A) | Non-ionic emulsifiers: | Trilaureth-4-Phosphate (alkyl polyglcol phosphoric acid ester | 2.0% by weight |
| | | Polyglyceryl-2-PEG-4-stearate | 6.0% by weight |
| | | Ceteareth-12 (PEG-12-cetyl stearyl ether) | 1.0% by weight |
| (B) | Oil portions: | Mineral Oil (Paraffin Oil) | 6.0% by weight |
| | | Avocado Oil | 1.0% by weight |
| | | Isopropyl Palmitate | 5.0% by weight |
| | | Jojoba Oil | 1.0% by weight |
| | | Octyldodecanol | 3.0% by weight |
| (C) | Consistency-providing agents: | Cetearyl Alcohol (Cetyl stearyl alcohol) | 2.0% by weight |
| | | Carbomer 940/Triethanolamine (Carboxyvinyl polymer; neutralized) | 0.7% by weight |
| (D) | Aqueous phase: | Water ad | 100.0% by weight |
| 2. | Viscosity | 340 mPas | |
| 3. | Propellant | $N_2O$ | |
| 4. | Properties of the product | | |
| | Foam density: | 0.1306 g/cm$^3$ | |
| | Average bubble size: | 10 μm | |
| | Stability: | >10 min. | |
| | Luster: | Shiny | |
| | Consistency: | Creamy | |

Example 1/2a

| 1. | Ingredients | | |
|---|---|---|---|
| (A) | Non-ionic emulsifiers: | Trilaureth-4-Phosphate | 2.0% by weight |
| | | Polyglyceryl-2-PEG-4-stearate | 6.0% by weight |
| | | Ceteareth-12 | 1.0% by weight |
| (B) | Oil portions: | Mineral Oil | 3.0% by weight |
| | | Avocado Oil | 1.0% by weight |
| | | Isopropyl Palmitate | 2.0% by weight |
| | | Jojoba Oil | 1.0% by weight |
| | | Octyldodecanol | 2.0% by weight |
| (C) | Consistency-providing agents: | Cetearyl Alcohol | 2.0% by weight |
| | | Carbomer 940/Triethanolamine | 0.7% by weight |
| (D) | Aqueous phase: | Water ad | 100.0% by weight |
| 2. | Viscosity | 295 mPas | |
| 3. | Propellant | $N_2O$ | |
| 4. | Properties of the product | | |
| | Foam density: | 0.1280 g/cm$^3$ | |
| | Average bubble size: | 10 μm | |
| | Stability: | >10 min. | |

Example 1/2b

| | | | |
|---|---|---|---|
| 1. | Ingredients | | |
| (A) | Non-ionic emulsifiers: | Trilaureth-4-Phosphate | 2.0% by weight |
| | | Polyglyceryl-2-PEG-4-stearate | 6.0% by weight |
| | | Ceteareth-12 | 1.0% by weight |
| (B) | Oil Portions: | Mineral Oil | 3.0% by weight |
| | | Avocado Oil | 1.0% by weight |
| | | Isopropyl Palmitate | 2.0% by weight |
| | | Jojoba Oil | 1.0% by weight |
| | | Octyldodecanol | 2.0% by weight |
| (C) | Consistency-providing agents: | Cetearyl Alcohol | 2.0% by weight |
| | | Carbomer 940/Triethanolamine | 0.7% by weight |
| (D) | Aqueous phase: | Water ad | 100.0% by weight |
| 2. | Viscosity | 295 mPas | |
| 3. | Propellant | $CO_2$ | |
| 4. | Properties of the Product | | |
| | Foam density: | 0.1523 g/cm³ | |
| | Average bubble size: | 10 μm | |
| | Stability: | >10 min. | |
| | Luster: | Shiny | |
| | Consistency: | Creamy | |

EXPLANATION OF EXAMPLES 1/1a, 1/2a, AND 1/2b

All these emulsions have a composition and viscosity according to the invention and contain ingredients which are in type and quantity suitable for cosmetic O/W-emulsions. They show good dermatological properties as well. The amount of the nonionic emulsifier The oil portion (B) and the viscosity for Example 1/1a is in the middle of the range. If you lower the percentage of oil portion, the resulting viscosity is also lower (compare Example 1/2a).

Example 1/2b shows the influence of $CO_2$. Delivered by dispenser, the resulting foam is more compact than if $N_2O$ is used (as in Example 1/2a), so that the foam density is higher.

Example 2/1a

| | | | |
|---|---|---|---|
| 1. | Ingredients | | |
| (A) | Non-ionic emulsifiers: | Steareth-2 (PEG-2-stearyl ether) | 4.5% by weight |
| | | Steareth-10 (PEG-10-stearyl ether) | 1.5% by weight |
| (B) | Oil portions: | Mineral Oil (Paraffin Oil) | 7.0% by weight |
| | | Isopropyl Palmitate | 7.0% by weight |
| | | Octyldodecanol | 6.5% by weight |
| (C) | Consistency-providing agent: | Cetyl Alcohol | 0.5% by weight |
| (D) | Aqueous phase: | Water ad | 100.0% by weight |
| 2. | Viscosity | 435 mPas | |
| 3. | Propellant | $N_2O$ | |
| 4. | Properties of the product | | |
| | Foam density: | 0.1514 g/cm³ | |
| | Average bubble size: | 15 μm | |
| | Stability: | >10 min. | |
| | Luster: | Shiny | |
| | Consistency: | Creamy | |

(A) used is at the higher limit of the prescribed range.

Example 2/1b

| | | | |
|---|---|---|---|
| 1. | Ingredients | | |
| (A) | Non-ionic emulsifiers: | Steareth-2 | 4.5% by weight |
| | | Steareth-10 | 1.5% by weight |
| (B) | Oil portions: | Mineral Oil | 7.0% by weight |
| | | Isopropyl Palmitate | 7.0% by weight |
| | | Octyldodecanol | 6.5% by weight |
| (C) | Consistency-providing agent: | Cetyl Alcohol | 0.5% by weight |
| (D) | Aqueous phase: | Water ad | 100.0% by weight |
| 2. | Viscosity | 435 mPas | |
| 3. | Propellant | $CO_2$ | |
| 4. | Properties of the product | | |
| | Foam density: | 0.1523 g/cm³ | |
| | Average bubble size: | 15 μm | |
| | Stability: | >10 min. | |

-continued

Example 2/1b

| | |
|---|---|
| Luster: | Shiny |
| Consistency: | Creamy |

Example 2/1c

| | | | |
|---|---|---|---|
| 1. | Ingredients | | |
| (A) | Non-ionic emulsifiers: | Steareth-2 | 4.5% by weight |
| | | Steareth-10 | 1.5% by weight |
| (B) | Oil portions: | Mineral Oil | 7.0% by weight |
| | | Isopropyl Palmitate | 7.0% by weight |
| | | Octyldodecanol | 6.5% by weight |
| (C) | Consistency-providing agent: | Cetyl Alcohol | 0.5% by weight |
| (D) | Aqueous phase: | Water ad | 100.0% by weight |
| 2. | Viscosity | 435 mPas | |
| 3. | Propellant | Fluorhydrocarbon F 12/114 40:60 | |
| 4. | Properties of the product | | |
| | Foam density: | 0.107 g/cm$^3$ | |
| | Average bubble size: | >20 μm | |
| | Stability: | >10 min. | |
| | Luster: | Dull | |
| | Consistency: | Like a shaving foam | |

Example 2/2a

| | | | |
|---|---|---|---|
| 1. | Ingredients | | |
| (A) | Non-ionic emulsifiers: | Steareth-2 | 4.5% by weight |
| | | Steareth-10 | 1.5% by weight |
| (B) | Oil portions: | Mineral Oil | 6.5% by weight |
| | | Isopropyl Palmitate | 5.0% by weight |
| | | Octyldodecanol | 6.0% by weight |
| | | Avocado Oil | 1.0% by weight |
| | | Jojoba Oil | 1.0% by weight |
| (C) | Consistency-providing agent: | Cetyl Alcohol | 1.5% by weight |
| (D) | Aqueous phase: | Water ad | 100.0% by weight |
| 2. | Viscosity | 560 mPas | |
| 3. | Propellant | $N_2O$ | |
| 4. | Properties of the product | | |
| | Foam density: | 0.1695 g/cm$^3$ | |
| | Average bubble size: | 10 μm | |
| | Stability: | >10 min. | |
| | Luster: | Shiny | |
| | Consistency: | Rigid, stiff | |

Example 2/2b

| | | | |
|---|---|---|---|
| 1. | Ingredients | | |
| (A) | Non-ionic emulsifiers: | Steareth-2 | 4.5% by weight |
| | | Steareth-10 | 1.5% by weight |
| (B) | Oil portions: | Mineral Oil | 6.5% by weight |
| | | Isopropyl Palmitate | 5.0% by weight |
| | | Octyldodecanol | 6.0% by weight |
| | | Avocado Oil | 1.0% by weight |
| | | Jojoba Oil | 1.0% by weight |
| (C) | Consistency-providing agent: | Cetyl Alcohol | 1.5% by weight |
| (D) | Aqueous phase: | Water ad | 100.0% by weight |
| 2. | Viscosity | 560 mPas | |
| 3. | Propellant | $CO_2$ | |
| 4. | Properties of the product | | |
| | Foam density: | 0.2480 g/cm$^3$ | |
| | Average bubble size: | 15 μm | |
| | Stability: | >10 min. | |
| | Luster: | Shiny | |
| | Consistency: | Rigid, stiff | |

EXPLANATION OF EXAMPLES 2/1a AND 2/2a

Example 2/1a has a composition and viscosity of the invention, and with ingredients in type and quantity suitable for cosmetic emulsions. The mid-range content of nonionic emulsifier (A), the high content of oil portion (B), and the low content of consistency-providing agent (C) leads to a viscosity of about 435 mPas. Use of more consistency-providing agent (1.5%) results in a higher viscosity (compare Example 2/2a) which is not satisfactory. The emulsion shows a viscosity which is too great and the delivered foam is too stiff. These examples show that there is a connection between the viscosity and the properties of the delivered foam. Because of their influence on each other, it is necessary to find the right proportions of the three components according to the cosmetic and dermatologic demands as well as to stability criteria.

If one uses $CO_2$ (2/1b, 2/2b) instead of $N_2O$ (2/1a, 2/2a), one obtains a delivered foam which shows an enlarged foam density. In case 2/1 the influence is not so remarkable. This effect can better be observed when the viscosity is too high to begin with, as in 2/2.

If one employs a liquified gas type propellant, such as a fluorohydrocarbon (2/1c), the delivered foam has no luster, is dull, and has the appearance of a shaving foam.

EXPLANATION OF EXAMPLE 3/1

This is simply another example, which shows an emulsion according to the invention, employing ingredients which are suitable for cosmetic emulsions.

| Example 4/1 | | | |
|---|---|---|---|
| 1. | Ingredients | | |
| (A) | Non-ionic emulsifier: | PEG-9-Stearate | 6.0% by weight |
| (B) | Oil portion: | Isopropyl Myristate | 6.0% by weight |
| (C) | Consistency-providing agent: | Cetyl Alcohol | 1.5% by weight |
| (D) | Aqueous phase: | Water ad | 100.0% by weight |
| 2. | Viscosity | 345 mPas | |
| 3. | Propellant | $N_2O$ | |
| 4. | Properties of the product | | |
| | Foam density: | 0.154 g/cm$^3$ | |
| | Average bubble size: | 15 μm | |
| | Stability: | >10 min. | |
| | Luster: | Shiny | |
| | Consistency: | Creamy | |

| Example 4/2 | | | |
|---|---|---|---|
| 1. | Ingredients | | |
| (A) | Non-ionic emulsifier: | PEG-9-Stearate | 6.0% by weight |
| (B) | Oil portion: | Isopropyl Myristate | 24.0% by weight |
| (C) | Consistency-providing agent: | Cetyl Alcohol | 1.5% by weight |
| (D) | Aqueous phase: | Water ad | 100.0% by weight |
| 2. | Viscosity | 300 mPas | |
| 3. | Propellant | $N_2O$ | |
| 4. | Properties of the product | | |
| | Foam density: | 0.172 g/cm$^3$ | |
| | Average bubble size: | 15 μm | |
| | Stability: | >10 min. | |
| | Luster: | Shiny | |
| | Consistency: | Too liquid | |

EXPLANATION OF EXAMPLES 4/1 AND 4/2

In this case only one ingredient for A, B and C is used in mid-range quantity.

Example 4/1 shows an emulsion according to the invention.

If the oil portion (C) is elevated (4/2), the composition is outside the claimed ranges. Although the viscosity is inside the invention, the delivered foam is too liquid.

| Example 3/1 | | | |
|---|---|---|---|
| 1. | Ingredients | | |
| (A) | Non-ionic emulsifiers: | PEG-20-glyceryl Stearate | 3.0% by weight |
| | | Glyceryl Stearate | 3.0% by weight |
| (B) | Oil portions: | Mineral Oil (Paraffin Oil) | 8.0% by weight |
| | | Isopropyl Palmitate | 8.0% by weight |
| | | Octyldodecanol | 3.7% by weight |
| (C) | Consistency-providing agents: | Cetearyl Alcohol (Cetyl stearyl alcohol) | 1.3% by weight |
| | | Carbomer 940/Triethanolamine (Carboxyvinyl Polymer; neutralized) | 0.7% by weight |
| (D) | Aqueous phase: | Water ad | 100.0% by weight |
| 2. | Viscosity | 340 mPas | |
| 3. | Propellant | $N_2O$ | |
| 4. | Properties of the product | | |
| | Foam density: | 0.1444 g/cm$^3$ | |
| | Average bubble size: | 10 μm | |
| | Stability: | >10 min. | |
| | Luster: | Shiny | |
| | Consistency: | Creamy | |

Example 5/1a

1. Ingredients

| | | | |
|---|---|---|---|
| (A) | Anionic emulsifiers: | TEA-Stearate (Triethanolamine Stearate) | 5.0% by weight |
| | | Sodium Laureth Sulphate (Sodium Lauryl Sulfate) | 0.25% by weight |
| | Non-ionic emulsifiers: | Polysorbate 20 (Sorbitan monolaurate) | 0.5% by weight |
| | | Lanolin Alcohol | 2.5% by weight |
| (B) | Oil portion: | Isopropyl Myristate | 0.5% by weight |
| (C) | Consistency-providing agents: | Cetyl Alcohol | 1.0% by weight |
| | | Talc | 2.0% by weight |
| (D) | Aqueous phase: | Water ad | 100.0% by weight |

2. Viscosity — 420 mPas
3. Propellant — $N_2O$
4. Properties of the product

| | |
|---|---|
| Foam density: | 0.1817 g/cm$^3$ |
| Average bubble size: | >20 μm |
| Stability: | 2 min. |
| Luster: | Shiny |
| Consistency: | Too liquid |

Example 5/1b

1. Ingredients

| | | | |
|---|---|---|---|
| (A) | Anionic emulsifiers: | TEA-Stearate | 5.0% by weight |
| | | Sodium Laureth Sulphate | 0.25% by weight |
| | Non-ionic emulsifiers: | Polysorbat 20 | 0.5% by weight |
| | | Lanolin Alcohol | 2.5% by weight |
| (B) | Oil portion: | Isopropyl Myristate | 0.5% by weight |
| (C) | Consistency-providing agents: | Cetyl Alcohol | 1.0% by weight |
| | | Talc | 2.0% by weight |
| (D) | Aqueous phase: | Water ad | 100.0% by weight |

2. Viscosity — 420 mPas
3. Propellant — $CO_2$
4. Properties of the product

| | |
|---|---|
| Foam density: | 0.3020 g/cm$^3$ |
| Average bubble size: | >20 μm |
| Stability: | 3 min. |
| Luster: | Shiny |
| Consistency: | Too liquid |

EXPLANATION OF EXAMPLES 5/1a AND 5/1b

Examples like these are described in the patent of Johnson & Son. Usually they describe formulations with anionic emulsifiers or combinations with non-ionics.

The results show that these emulsions cannot be delivered by compressed gases. The appearance of the delivered product does not conform to that of the present invention although the viscosity is in the proper range (5/1a). The use of $N_2O$ alone leads to a foam which is too liquid, as does the use of $CO_2$ (5/1b).

It is necessary to mix two types of propellants as described in the U.S. Pat. No. 3,970,584 with this type of emulsion composition.

The resulting foam product has an appearance which is not within the proposed product properties according to the present invention.

Example 6/1

1. Ingredients

| | | | |
|---|---|---|---|
| (A) | Anionic emulsifiers: | TEA-Stearate | 5.0% by weight |
| | | Sodium Laureth Sulphate | 0.25% by weight |
| | Non-ionic emulsifiers: | Sorbitan Stearate | 0.5% by weight |
| | | Lanolin Alcohol | 5.0% by weight |
| (B) | Oil portion: | Isopropyl Myristate | 10.0% by weight |
| (C) | Consistency-providing agent: | Cetyl Alcohol | 0.5% by weight |
| (D) | Aqueous phase: | Water ad | 100.0% by weight |

2. Viscosity — 900 mPas
3. Propellant — $N_2O$
4. Properties of the product

| | |
|---|---|
| Foam density: | 0.1866 g/cm$^3$ |
| Average bubble size: | >20 μm |
| Stability: | 2 min. |
| Luster: | Shiny |
| Consistency: | Too liquid |

EXPLANATION OF EXAMPLE 6/1

This example is also given in the S. C. Johnson & Son Patent. In comparison to Example 5, the viscosity has been increased to 900 mPas. Even this alteration does not lead to a foamed product which is sufficiently stable or creamy.

Example 7/1a

| 1. Ingredients | | |
|---|---|---|
| (A) Non-ionic emulsifier: | Ceteareth-12 (PEG-12-cetyl stearyl ether) | 2.0% by weight |
| (B) Oil portions: | Mineral Oil (Paraffin Oil) | 7.0% by weight |
| | Isopropyl Palmitate | 7.4% by weight |
| | Octyldodecanol | 7.4% by weight |
| (C) Consistency-providing agents: | Stearic Acid | 3.5% by weight |
| | Cetearyl Alcohol (Cetyl stearyl alcohol) | 0.7% by weight |
| (D) Aqueous phase: | Water ad | 100.0% by weight |
| 2. Viscosity | 110 mPas | |
| 3. Propellant | $N_2O$ | |
| 4. Properties of the product | | |
| Foam density: | 0.1204 g/cm$^3$ | |
| Average bubble size: | 15 μm | |
| Stability: | 1 min. | |
| Luster: | Shiny | |
| Consistency: | Too liquid | |

Example 7/1b

| 1. Ingredients | | |
|---|---|---|
| (A) Non-ionic emulsifier: | Ceteareth-12 | 2.0% by weight |
| (B) Oil portions: | Mineral Oil | 7.0% by weight |
| | Isopropyl Palmitate | 7.4% by weight |
| | Octyldodecanol | 7.4% by weight |
| (C) Consistency-providing agents: | Stearic Acid | 3.5% by weight |
| | Cetearyl Alcohol | 0.7% by weight |
| (D) Aqueous phase: | Water ad | 100.0% by weight |
| 2. Viscosity | 110 mPas | |
| 3. Propellant | $CO_2$ | |
| 4. Properties of the product | | |
| Foam density: | 0.1673 g/cm$^3$ | |
| Average bubble size: | 15 μm | |
| Stability: | 0.5 min. | |
| Luster: | Shiny | |
| Consistency: | Too liquid | |

Example 7/2

| 1. Ingredients | | |
|---|---|---|
| (A) Non-ionic emulsifier: | Ceteareth-12 | 2.0% by weight |
| (B) Oil portions: | Mineral Oil | 4.0% by weight |
| | Isopropyl Palmitate | 3.0% by weight |
| | Octyldodecanol | 3.0% by weight |
| (C) Consistency-providing agents: | Stearic Acid | 2.5% by weight |
| | Cetearyl Alcohol | 1.0% by weight |
| (D) Aqueous phase: | Water ad | 100.0% by weight |
| 2. Viscosity | 230 mPas | |
| 3. Propellant | $N_2O$ | |
| 4. Properties of the product | | |
| Foam density: | 0.153 g/cm$^3$ | |
| Average bubble size: | 15 μm | |
| Stability: | >10 min. | |
| Luster: | Shiny | |
| Consistency: | Creamy | |

EXPLANATION OF EXAMPLES 7/1 AND 7/2

Example 7/1 is not an emulsion composition of the invention, both the oil portion and the viscosity being outside the prescribed ranges. Neither compressed gas ($N_2O$, $CO_2$) will work. By varying the components B and C to get a stable emulsion system, a formula (7/2) is found which has the right viscosity, and product-emulsion as well as foam properties are within the range of the present invention.

Example 8/1a

| 1. Ingredients | | |
|---|---|---|
| (A) Non-ionic emulsifiers: | Glyceryl Stearate | 5.0% by weight |
| | Ceteareth-12 | 3.0% by weight |
| (B) Oil portions: | Mineral Oil | 7.0% by weight |
| | Isopropyl Palmitate | 7.0% by weight |
| | Octyldodecanol | 4.2% by weight |
| (C) Consistency-providing agent: | Cetearyl Alcohol | 0.8% by weight |
| (D) Aqueous phase: | Water ad | 100.0% by weight |

Example 8/1a -continued

| | |
|---|---|
| 2. Viscosity | 130 mPas |
| 3. Propellant | $N_2O$ |
| 4. Properties of the product | |
| Foam density: | 0.1163 g/cm³ |
| Average bubble size: | >20 μm |
| Stability: | 2 min. |
| Luster: | Shiny |
| Consistency: | Too liquid |

Example 8/1b

| | | |
|---|---|---|
| 1. Ingredients | | |
| (A) Non-ionic emulsifiers: | Glyceryl Stearate | 5.0% by weight |
| | Ceteareth-12 | 3.0% by weight |
| (B) Oil portions: | Mineral Oil | 7.0% by weight |
| | Isopropyl Palmitate | 7.0% by weight |
| | Octyldodecanol | 4.2% by weight |
| (C) Consistency-providing agent: | Cetearyl Alcohol | 0.8% by weight |
| (D) Aqueous phase: | Water ad | 100.0% by weight |
| 2. Viscosity | 130 mPas | |
| 3. Propellant | $CO_2$ | |
| 4. Properties of the product | | |
| Foam density: | 0.1570 g/cm³ | |
| Average bubble size: | 15 μm | |
| Stability: | 2 min. | |
| Luster: | Shiny | |
| Consistency: | Too liquid | |

EXPLANATION OF EXAMPLES 8/1a AND 8/1b

The formula percentages are inside the claimed range of the invention but the resulting viscosity is too low. The foam delivered is not satisfactory. This fact is not dependent upon the pressurized propellant used (a=$N_2O$, b=$CO_2$).

Example 9/1

| | | |
|---|---|---|
| 1. Ingredients | | |
| (A) Non-ionic emulsifier: | Polyglycol Stearic Acid Ester* | 5.0% by weight |
| (B) Oil portions: | Mineral Oil | 7.0% by weight |
| | Isopropyl Palmitate | 7.0% by weight |
| | Octyldodecanol | 7.0% by weight |
| (C) Consistency-providing agent: | Cetyl Alcohol | 1.0% by weight |
| (D) Aqueous phase: | Water ad | 100.0% by weight |
| 2. Viscosity | 70 mPas | |
| 3. Propellant | $N_2O$ | |
| 4. Properties of the product | | |
| Foam density: | 0.1429 g/cm³ | |
| Average bubble size: | >20 μm | |
| Stability: | 1 min. | |
| Luster: | Shiny | |
| Consistency: | Too liquid | |

*not listed in the CTFA-Dictionary

Example 9/2

| | | |
|---|---|---|
| 1. Ingredients | | |
| (A) Non-ionic emulsifier: | Polyglycol Stearic Acid Ester* | 5.0% by weight |
| (B) Oil portions: | Mineral Oil | 5.0% by weight |
| | Isopropyl Palmitate | 4.0% by weight |
| | Octyldodecanol | 4.0% by weight |
| (C) Consistency-providing agent: | Cetyl Alcohol | 2.0% by weight |
| (D) Aqueous phase: | Water ad | 100.0% by weight |
| 2. Viscosity | 445 mPas | |
| 3. Propellant | $N_2O$ | |
| 4. Properties of the product | | |
| Foam density: | 0.157 g/cm³ | |
| Average bubble size: | 15 μm | |
| Stability: | >10 min. | |
| Luster: | Shiny | |
| Consistency: | Creamy | |

*not listed in the CTFA-Dictionary

Example 9/3

| 1. Ingredients: | | |
|---|---|---|
| Non-ionic wetting agent: | Polyglyceryl-2-PEG-4-stearate | 2.0% by weight |
| Cationic wetting agent: | Distearyl dimethyl ammonium chloride | 1.0% by weight |
| Oil portions: | Paraffin oil | 7.0% by weight |
| | Octyl dodecanol | 8.0% by weight |
| | Isopropyl palmitate | 7.5% by weight |
| Consistency-providing agent: | Cetyl alcohol | 0.5% by weight |
| Aqueous phase: | Water ad | 100.0% by weight |
| 2. Viscosity: | 160 mPas | |
| 3. Propellant: | $N_2O$ | |
| 4. Foam density: | 0.1773 g/cm$^3$ | |
| 5. Average bubble size: | 15 μm | |
| 6. Stability: | >10 min. | |
| Luster: | Shiny | |
| Consistency: | Rigid | |

EXPLANATION OF EXAMPLES 9/1, 9/2 AND 9/3

The formulation of Example 9/1 shows the same characteristics as Example 8. The composition conforms to the claimed range of the ingredients but the viscosity is too low (9/1). If the formulation is altered to bring the viscosity inside the necessary range (about 445 mPas in 9/2), a mousse according to the invention can be delivered by nitrous oxide.

The formulation of Example 9/3 is an example of another composition outside the scope of the present invention, and gives an obviously unsatisfactory product and result.

From the foregoing Tabulations and Explanations, it is apparent that the compositions of the present invention are foamable cream emulsions which, upon activation by the included propellant in a suitable dispensing container, are productive of an extremely high quality cosmetic mousse.

In conclusion, from the foregoing Examples, Tabulations, and Discussion it is apparent that the present invention, which involves the employment of certain well-defined but relatively limited ingredients within certain relatively specific parameters or ranges, provides novel foamable compositions which are useful in producing a superb shiny, stable, and creamy cosmetic mousse, upon activation of the propellant contained therein simply by releasing the same to the external or ambient atmosphere in usual manner through a usual dispensing nozzle, and which are therefore useful as cosmetic mousse-producing foamable creams, having the said desirable, highly advantageous, and unpredictable properties.

It is to be understood that the invention is not to be limited to the exact details of operation, or to the exact compounds, compositions, methods, procedures, or embodiments shown and described, as obvious modifications and equivalents will be apparent to one skilled in the art, and the invention is therefore to be limited only by the full scope of the appended claims.

We claim:

1. A foamable cream, suitable for forming a cosmetic mousse, comprising an oil-in-water cream emulsion and a propellant therein, characterized in that the cream emulsion prior to admixture with the propellant consists essentially of a mixture of between about 2 and 9 percent by weight of a dermatologically-acceptable non-ionic emulsifying agent, between about 4.5 and 21 percent by weight of an oil portion, and between about 0.5 and 4.5 percent by weight of a consistency-providing agent, the balance being water to 100 percent by weight, has a viscosity between about 200 and 500 mPas, and by the fact that the propellant consists essentially of nitrous oxide or carbon dioxide.

2. A composition according to claim 1 characterized in that the propellant consists essentially of nitrous oxide.

3. A cosmetic mousse produced from the composition of claim 2 wherein the bubble size is between about 4 and 20 μm and the foam density is between about 0.1 and 0.16 g/cm$^3$.

4. A composition of claim 1 wherein the propellant is present in an amount between about one and four percent by weight of the propellant-containing emulsion.

5. A composition of claim 4 wherein the composition is under a pressure between about 100 and 150 psi.

6. A composition of claim 4 wherein the propellant is $CO_2$ in amount between about 1.2 and 1.7 percent.

7. A composition of claim 4 wherein the propellant is $N_2O$ in amount between about 2 and 3.2 percent.

* * * * *

UNITED STATES PATENT AND TRADEMARK OFFICE
CERTIFICATE OF CORRECTION

PATENT NO. : 4,808,388
DATED : February 28, 1989
INVENTOR(S) : Rolf D. Beutler, Thomas Wimmer and Gunhild Angst It is certified that error appears in the above-identified patent and that said Letters Patent is hereby corrected as shown below:

Col. 1, line 46; "with" should read -- within --
Col. 1, line 63; "propellent," should read -- propellant, --
Col. 2, line 43; "porton" should read -- portion --
Col. 2, line 47; "forom" should read -- from --
Col. 2, line 56; "propellent" should read -- propellant --
Col. 3, lines 9 & 10; "propellent" should read -- propellant --
Col. 4, line 5; "emuslion" should read -- emulsion --
Col. 5, line 3; "REPESENTATIVE" should read -- REPRESENTATIVE --
Cols. 5 & 6, under "Example 1/1a", Column 3, line 1; "polyglcol" should read -- polyglycol --

Signed and Sealed this

Fifth Day of December, 1989

Attest:

JEFFREY M. SAMUELS

*Attesting Officer*   *Acting Commissioner of Patents and Trademarks*